United States Patent [19]

Bach et al.

[11] Patent Number: 5,266,729
[45] Date of Patent: Nov. 30, 1993

[54] PROCESS FOR THE PREPARATION OF TRICYCLO [5.2.02,6]DECAN-8(9)-ONE

[75] Inventors: Hanswilhelm Bach, Duisburg; Werner Kohl, Oberhausen; Gregor Deckers, Xanten; Detlef Kampmann, Bochum; Claus Kniep, Oberhausen, all of

[73] Assignee: Hoechst Aktiengesellschaft, Fed. Rep. of Germany

[21] Appl. No.: 931,891

[22] Filed: Aug. 18, 1992

Related U.S. Application Data

[63] Continuation of Ser. No. 743,197, Aug. 9, 1991, abandoned.

[30] Foreign Application Priority Data

Aug. 11, 1990 [DE]  Fed. Rep. of Germany ....... 4025526

[51] Int. Cl.$^5$ ............................................. C07C 45/29
[52] U.S. Cl. .................................................... 568/361
[58] Field of Search ......................................... 568/361

[56] References Cited

U.S. PATENT DOCUMENTS

| | | | |
|---|---|---|---|
| 2,849,489 | 8/1958 | Buchner et al. | 568/361 |
| 4,304,943 | 12/1981 | Bjornson | 568/361 |
| 4,415,477 | 11/1983 | Rozovsky et al. | 568/361 |

FOREIGN PATENT DOCUMENTS

| | | | |
|---|---|---|---|
| 953076 | 11/1956 | Fed. Rep. of Germany | 568/361 |
| 2047437 | 5/1972 | Fed. Rep. of Germany | |

*Primary Examiner*—James H. Reamer
*Attorney, Agent, or Firm*—Jordan B. Bierman

[57] ABSTRACT

A process for the preparation of tricyclo[5.2.1.0$^{2,6}$]decan-8(9)-one by the conversion of 8(9)-hydroxytricyclo[5.2.1.0$^{2,6}$]dec-3-ene by means of a supported catalyst containing nickel and magnesium oxide at elevated temperature and, if necessary, at elevated pressure.

17 Claims, No Drawings

PROCESS FOR THE PREPARATION OF TRICYCLO [5.2.02,6]DECAN-8(9)-ONE

This application is a continuation of application number 07/743,197, filed Aug. 9, 1991, now abandoned.

This Application claims the benefit of the priority of German Application 40 25 526.3, filed Aug. 11, 1990.

SUMMARY OF THE INVENTION

The present invention relates to a process for the preparation of tricyclo[5.2.1.0$^{2,6}$]decan-8(9)-one by the conversion of 8(9)-hydroxytricyclo[5.2.1.0$^{2,6}$]dec-3-ene by means of supported catalyst containing nickel and magnesium oxide at elevated temperatures and, if necessary, at elevated pressures.

In all probability, this conversion is an intramoleculoar transposition of hydrogen in which the hydroxyl group located in the 8-position or 9-position is converted with loss of hydrogen into the corresponding keto group, and the liberated hydrogen becomes attached to the carbon-carbon double bond located in the 3-position. The equation below illustrates the reaction according to the invention, which results in the formation of a ketone with the simultaneous elimination of the carbon-carbon double bond present in the molecule.

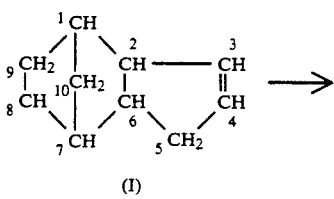

(I)

8(9)-hydroxytricyclo[5.2.1.0$^{2,6}$]dec-3-ene

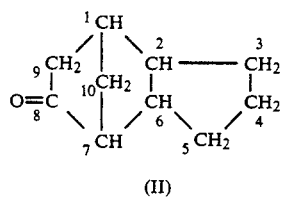

(II)

tricyclo[5.2.1.0$^{2,6}$]decan-8(9)-one

The unsaturated alcohol (I) required as the starting material for the reaction can be prepared, even on an industrial scale, by the addition reaction of water with dicyclopentadiene. The catalysts used are preferably $H_2SO_4$ or cation exchangers. The saturated tricyclic ketone (II) can, in the broadest sense, be considered one of the terpene ketones. By virtue of its characteristic structure and typical odor, it is suitable for use as a component for the preparation of perfumes.

This applies both to the ketone itself and to its readily preparable derivatives. As a consequence of its use as a perfume, the purity of the saturated tricyclic ketone (II) has to meet strict requirements, in which connection it is advantageous that unreacted alcohol (I) can be removed by fractional distillation and re-used for a further reaction.

German Patent 953,076 discloses a process for the conversion of 8-hydroxytricyclodec-4-ene, which may be equated with the unsaturated tricyclic alcohol (I), into 8-ketotricyclodecane, which corresponds to the saturated tricyclic ketone (II). The reaction is carried out at temperatures of 100° to 250° C. by means of metals of the VIIIth and/or 1st subgroup of the Periodic Table (IUPAC version) which are activated by metal oxides of the 2nd main group of the Periodic Table and, if appropriate, are deposited on inert supports, preferably on kieselguhr. It has been found, however, that not every one of these catalysts, particularly not every nickel/magnesium oxide/kieselguhr catalyst—as proved by tests—is equally suitable for carrying out this reaction.

It was therefore the object of the invention to develop a process which ensures, by means of a catalyst readily accessible in industry, that the reaction always proceeds to a reproducible extent and, as far as possible, with the avoidance of undesirable byproducts.

DETAILED DESCRIPTION OF THE INVENTION

This object is achieved by means of a process for the preparation of tricyclo[5.2.1.0$^{2,6}$]decan-8(9)-one by the conversion of 8(9)-hydroxytricyclo[5.2.1.0$^{2,6}$]dec-3-ene by means of a supported catalyst containing nickel and magnesium oxide at elevated temperatures and, if necessary, at elevated pressures. The process is one wherein the supported catalyst contains magnesium and nickel in a molar ratio of (0.0075 to 0.075): 1 and 17.0 to 60.0 grams of a water-insoluble support per mol of Ni. The active nickel metal surface area is 110 to 180 m$^2$/g of nickel, and 65 to 97% of the BET total surface area is composed of pores having a radius $r_p \leq 2.5$ nm.

An essential characteristic of the supported catalyst used is the narrow distribution of the pore radii, expressed by a high proportion of the BET total surface area which originates from pores having a radius $r_p \leq 2.5$ nm. The BET total surface area is 160 to 450, in particular 180 to 380 and most preferably 200 to 350, m$^2$/g of catalyst. The BET total surface area is to be understood as meaning the surface area determined by the absorption of nitrogen by the method of Brunauer, Emmett and Teller (BET) described in J. Amer. Chem. Soc. 60, (1938) 309. As a result of the above-mentioned narrow distribution of the pore radii, having a range $r_p \leq 2.5$ nm as its focal point, the catalyst acquires special properties which result in an increase in the activity and an improvement in the selectivity of conversion of the reaction on which the process according to the invention is based.

A further characteristic of the catalyst is its composition, expressed as the molar ratio of Mg to Ni. For the sake of completeness, attention is drawn to the following definition. 1 mol of Mg or 1 mol of Mg$^{2+}$ corresponds to 24.305 g of Mg or 24.305 g of Mg$^{2+}$, and 1 mol of Ni or 1 mol of Ni$^{2+}$ corresponds to 58.71 g of Ni or 58.71 g of Ni$^{2+}$. In the reduced state of the catalyst, magnesium is present as Mg$^{2+}$ and nickel is predominantly or almost completely present in the form of metal. More precisely formulated, the molar ratio is thus to be understood as meaning the ratio of mols of Mg$^{2+}$: (mols of Ni+mols of unreduced Ni$^{2+}$).

As already mentioned above, in the reduced form the catalyst contains Mg and Ni in a molar ratio of (0.0075 to 0.075):1. It has proved particularly suitable to select an Mg:Ni molar ratio of (0.015 to 0.060):1, in particular (0.022 to 0.055):1.

The composition of the new catalyst is also determined by the ratio in parts by weight of the water-insoluble support to Ni, which once again means the sum of the mols of metallic nickel and mols of Ni$^{2+}$.

Various water-insoluble materials are suitable for use as supports. These include silicates, such as Ca silicate, Mg silicate, Al silicate, $Al_2O_3$, $SiO_2$, kieselguhr and mixtures thereof. Supports which should be singled out as particularly useful are Mg silicates (in particular in the form of pumice stone), $Al_2O_3$, $SiO_2$, kieselguhr and mixtures thereof, especially pumice stone, $Al_2O_3$, kieselguhr. and mixtures thereof, most preferably $SiO_2$ and/or kieselguhr. Kieselguhr has proved most suitable of all. The support material should usually be in a finely divided form. Its particles should have a particle size of 1 to 30, in particular 2 to 25 and preferably 3 to 20, μm.

The catalyst contains 17.0 to 60.0, in particular 25 to 50 and preferably 30 to 40, grams of support per mol of Ni. As already mentioned above, a mol of Ni is to be understood as meaning the sum of nickel in the reduced and unreduced forms.

The active nickel metal surface area of the catalyst is 110 to 180, in particular 125 to 160 and preferably 130 to 150, $m^2/g$ of Ni. Its determination is carried out by a method modelled on a method described in greater detail in the Journal of Catalysis 81, (1983) 204 and 96 (1985) 517, by measuring the amount of hydrogen absorbed by chemisorption at 20° C.

Of the entire BET surface area, 65% to 97%, in particular 70% to 95%, and especially 75% to 95%, is composed of pores having a radius $r_p \leq 2.5$ nm (25 Å). The radius of the pores is determined by a method described in greater detail in S. J. Gregg and K. S. W. Sing, Adsorption Surface Area and Porosity (Academic Press, New York-London 1967), pages 160 to 182.

The catalyst is also distinguished by the fact that 60 to 95%, in particular 70 to 95% and preferably 73 to 90%, of the BET total surface area is composed of pores having a radius $r_p$ of 1.5 to 2.5 nm (15 to 25 Å). Pores having a radius of $r_p$ of 1.8 to 2.5 nm (18 to 25 Å) form 35 to 85%, in particular 45 to 76% and preferably 50 to 70%, of the BET total surface area.

The starting material for the process for the preparation of the catalysts used is an aqueous solution containing nickel salts and magnesium salts. This mixed salt solution contains 10 to 100, in particular 20 to 80 and preferably 30 to 50, g of Ni/l. Its magnesium content corresponds to 0.2 to 15, in particular 0.5 to 12 and preferably 1 to 10, g of MgO/l.

The mixed salt solution is prepared by dissolving water-soluble, inorganic, organic or complex salts of nickel and magnesium in water. Salts which are very suitable are the sulfates, chlorides, acetates, propionates, butyrates and nitrates. It has proved particularly suitable to employ nickel and magnesium in the form of their sulfates, chlorides, acetates and nitrates, preferably in the form of their nitrates. In order to prevent undesired hydrolysis and to exert an advantageous influence on the precipitation, it is advisable to have an excess of free acid in the mixed salt solution.

The mixed salt solution is fed to a support suspended in water, separately from, but at the same time as, an aqueous solution of a basic precipitant. An aqueous solution of a basic compound is used as the precipitant. An aqueous solution containing $Na_2CO_3$ and/or $NaHCO_3$ is particularly suitable. The precipitant should have a pH of 7.5 to 13, in particular 8 to 12, and preferably 9 to 11. The aqueous solution contains 0.1 to 4.0, in particular 0.6 to 3.0 and preferably 1.6 to 2.4, equivalents of basic compound per liter of solution. Very good results are achieved using aqueous solutions containing 0.3 to 1.5, in particular 0.8 to 1.2, mol of alkali metal carbonate per liter of solution.

In order to ensure that the precipitation is as complete as possible and, at the same time, obtain a particularly homogeneous co-precipitate composed of basic nickel and magnesium compounds, the basic compound is employed in a slight excess relative to the amount of basic compound required for the complete precipitation of Ni and Mg. The precipitation is brought about by feeding the mixed salt solution and the precipitant with mixing separately, but simultaneously, continuously or batchwise to a support material which is suspended in water and is suitable for the preparation of the catalyst. The substances already mentioned, namely silicates of calcium, magnesium and/or aluminium, $Al_2O_3$, $SiO_2$ and/or kieselguhr, especially kieselguhr, can be used as the support material.

The precipitation of the co-precipitate composed of basic nickel and magnesium compounds is brought about by a relatively slow addition of the mixed salt solution and the precipitant. The precipitation time should be at least 10, in particular at least 15 and preferably at least 20, minutes.

The precipitation is carried out at a constant pH within a pH range from 6 to 8.5, especially 6.5 to 7.8. Fluctuations in the pH should be kept as small as possible. The precipitation is carried out at temperatures above 80° C., particularly in a range from 90° to 110° C., preferably 95° to 105° C.

The co-precipitate contains magnesium and nickel in a molar ratio of (0.02 to 0.25):1, in particular (0.03 to 0.2):1 and preferably (0.035 to 0.1): 1. The coprecipitate is separated off from the mother liquor when the precipitation is complete. This can be effected by decantation and/or filtration.

The co-precipitate is then washed with water, in the course of which the basic magnesium compounds contained in the co-precipitate, as well as the constituents present in a soluble state, for example $Na^+$ and $NO_3^-$ are leached out from the co-precipitate. The result of this is that the molar ratio of magnesium to nickel is altered and is shifted to lower values because of the decrease in magnesium. Washing is carried out at relatively high temperatures of 60° to 90° C., in particular 65° to 85° C. and preferably 70° to 80° C. The duration of the washing process must be adequately long. It should be at least 60, in particular at least 80 and preferably at least 90, minutes. If desired, the washed catalyst composition can be brought into an agglomerated form. There are proven processes which can be used for this, for example, strand extrusion.

Drying is carried out at elevated temperatures, preferably in stages at increasing temperatures. It proves adequate to carry out the drying at temperatures of 50° to 120° C., in particular 55° to 100° C. and preferably 60° to 90° C., using customary processes, such as laying out the material to be dried in a fixed bed or in a moving bed, for example as fluidized bed.

The reduction of the catalyst composition is effected by means of hydrogen or gas mixtures containing hydrogen at temperatures of 260° to 400° C., in particular 280° to 360° C.

The process according to the invention is carried out at 150° to 300° C., in particular 180° to 280° C. and preferably 200° to 260° C., and under a pressure of 0.1 to 1.0, in particular 0.15 to 0.8 and preferably 0.15 to 0.6, MPa.

The process according to the invention can be carried out either continuously or batchwise. In the continuous procedure a pressure-resistant tubular reactor containing the catalyst in agglomerated form, for example laid out as a fixed bed, is usually employed. The unsaturated tricyclic alcohol (I) is fed to the reactor either at the top or at the bottom. Depending on the mode of addition, this is known as a trickle or liquid-phase operation.

However, it is also possible to dispense with the use of expensive tubular reactors and to carry out the reaction in, for example, stirred vessels or loop reactors. In this case the reaction takes place in the presence of a suspended catalyst; this process is also known as suspension operation. In this case the catalyst is employed in an agglomerated form, for example, as filaments, tablets, pellets, or granules, but also in a comminuted state or as powder. The particle size should neither be too coarse nor too fine. Excessively large catalyst particles have a disadvantageous effect because of their relatively small surface area available for the reaction. On the other hand, finely divided catalysts prove reactive because of a relatively large surface area, but their small particle size impedes their removal, which is to be carried out by sedimentation, centrifugation, or filtration. The removal of the catalyst containing nickel after the conclusion of the reaction is necessary in order to avoid undesirable side reactions during preparation. For example, even small amounts of nickel can result in rearrangements and cleavages during distillation. The by-products thus formed contaminate the desired saturated, tricyclic ketone (II).

The suspension procedure described above is particularly suitable for carrying out the process according to the invention batchwise. In this case the catalyst is suspended in a solvent before the start of the reaction. This solvent should be inert toward the reaction which takes place, i.e. it must not interfere in the intramolecular transposition of hydrogen and must also not react with the alcohol to be reacted and its reaction product, namely the ketone. Suitable solvents are aliphatic, hydrocarbons cycloaliphatic hydrocarbons, aromatic hydrocarbons, ethers and/or alcohols. Solvents with too low boiling points should, however, not be selected, in order to prevent a build-up of pressure during the reaction, which takes place at relatively high temperatures.

In a preferred variant of the inventive process, a solvent of the type mentioned above is omitted and, instead, the catalyst is suspended in the starting material (I), in the reaction mixture, and/or the reaction product (II).

In the batchwise procedure the total amount of the unsaturated tricyclic alcohol (I) to be reacted is added to the suspended catalyst, and the mixture is heated to the desired temperature with stirring and allowed to react. When the reaction is complete the mixture is cooled and the reaction product is separated from the catalyst. The catalyst which has been separated off can be employed again in the reaction.

Suspended hydrogenation catalysts usually disintegrate to an increasing extent on prolonged use. The finely divided particles resulting from this are not desirable since, as mentioned previously, they make it more difficult to remove the suspended catalyst after the reaction. The suspended catalyst is usually removed by sedimentation and/or centrifugation and/or filtration. However, the finer the catalyst particles, the more difficult it is to remove them from the reaction mixture. A smaller particle size also means a reduced rate of sedimentation, which also has a disadvantageous effect on centrifugation. If filtration is used for removing the catalyst, particularly small particles have a strong tendency to rapidly block the filtration unit by obstruction of the filter pores. This results in an increase of pressure in the equipment, with the result that the filtration must be interrupted in order to remove the blockage.

The hydrogenation catalyst used has a relatively low tendency to disintegrate and can therefore be removed from the reaction mixture without difficulty even when employed repeatedly. For this reason it has proved suitable to employ the catalyst in a pre-comminuted state.

The following examples illustrate the invention, without limiting it.

EXAMPLE

As the starting materials 400 g of 8(9)-hydroxytricyclo[5.2.1.0$^{2,6}$]dec-3-ene are placed in a 1 liter autoclave equipped with a stirrer which has been flushed with $N_2$. 5% by weight of a catalyst containing, per mol of nickel, 38 g of support (kieselguhr) and having an Mg:Ni molar ratio of 0.04:1, an active nickel metal surface area of 130 m$^2$/g of nickel and a BET total surface area of 200 m$^2$/g of catalyst, 90% of the BET total surface area being composed of pores having a radius $r_p \leq 2.5$ nm (25 Å), are introduced (based on the 8(9)-hydroxytricyclo[5.2.1.0$^{2,6}$]dec-3-ene). The mixture is then heated to 235° C. During the reaction time of 10 hours a pressure of 0.25 to 0.5 MPa is set up.

The conversion, relative to alcohol employed, is >99.9% and the selectivity of conversion in respect of the formation of tricyclo[5.2.1.0$^{2,6}$]decan-8(9)-one is 92.5%. Since only traces of the unsaturated ketone (tricyclo[5.2.1.0$^{2,6}$]dec-3-en-8(9)-one are formed, an aftertreatment of the reaction product—as indicated in Comparison Test 3—is not necessary.

COMPARISON TEST 1

The procedure is as indicated in the Example. 5% by weight of catalyst, relative to the alcohol, is employed. Per mol of nickel, the catalyst contains 26 g of support (kieselguhr) and has an Mg:Ni molar ratio of 0.12:1 and an active nickel metal surface area of 65 m$^2$/g of nickel. The reaction temperature is 235° C. A pressure of 0.16 to 0.44 MPa is set up during the reaction time of 10 hours. The conversion, relative to alcohol employed, is 38.5% and the selectivity of conversion with respect to the formation of tricyclo[5.2.1.0$^{2,6}$]decan-8(9)-one is only 7%. The remainder of the reaction mixture contains, besides unreacted starting material, mainly 8(9)-hydroxytricyclo[5.2.1.0$^{2,6}$]decane and tricyclo[5.2.1.0$^{2,6}$]dec-3-en-8(9)-one, i.e. a saturated alcohol and an unsaturated ketone.

COMPARISON TEST 2

The procedure is as indicated in the Example. Relative to the alcohol, 5% by weight of catalyst is employed. Per mol of nickel, the catalyst contains 33 g of support (kieselguhr) and has an Mg:Ni molar ratio of 0.12:1 and an active nickel metal surface area of 86 m$^2$/g of nickel. The reaction temperature is 235° C. A pressure of 0.2 to 0.4 MPa is set up during the reaction time of 10 hours.

The conversion, relative to the alcohol employed, is 67.1% and the selectivity of conversion with respect to the formation of tricyclo[5.2.1.0$^{2,6}$]decan-8(9)-one is only 21%. The remainder of the reaction mixture contains the same constituents as in Comparison Test 1.

COMPARISON TEST 3

The procedure is as indicated in the Example. Relative to the alcohol, 5% by weight of catalyst is employed. Per mole of nickel, the catalyst contains 33 g of support (kieselguhr) and has an Mg:Ni molar ratio of 0.08:1 and an active metal surface area of 90 m$^2$/g of nickel. The reaction temperature is 250° C. A pressure of 0.25 to 0.4 MPa is set up during the reaction time of 10 hours.

The conversion, relative to alcohol employed, is >99.9%, however, the selectivity of conversion with respect to the formation of tricyclo[5.2.1.0$^{2,6}$]decan-8(9)-one is only 81.5%.

Owing to the presence of the unsaturated ketone (tricyclo[5.2.1.0$^{2,6}$]dec-3-en-8(9)-one, the boiling point of which is very close to that of the desired product, the attempt to separate the desired ketone from the reaction product by distillation is not successful. In order to obtain the product of value (tricyclo[5.2.1.0$^{2,6}$]decan-8(9)-one) in the necessary purity, the reaction mixture must be subjected to a separate after-hydrogenation in the presence of a noble metal catalyst.

What we claim is:

1. A process for the preparation of tricyclo[5.2.1.0$^{2,6}$]decan-8(9)-one by conversion of 8(9)-hydroxytricyclo[5.2.1.0$^{2,6}$]dec-3-ene by a supported catalyst containing nickel and magnesium oxide at elevated temperature wherein said supported catalyst contains Mg and Ni in a molar ratio of (0.0075 to 0.075):1 and there is 17.0 to 60.0 grams of a water-insoluble support per mole of Ni, an active nickel metal surface area being 110 to 180 m$^2$/g of Ni, and 65 to 97% of a BET total surface area is composed of pores having a radius $r_p \leq 2.5$ nm.

2. The process of claim 1 wherein said conversion is carried out at elevated pressure.

3. The process of claim 1 wherein said catalyst has a BET total surface area of 160 to 450 m$^2$/g of said catalyst.

4. The process of claim 3 wherein said BET total surface area is 180 to 380 m$^2$/g of said catalyst.

5. The process of claim 4 wherein said BET total surface area is 200 to 350 m$^2$/g of said catalyst.

6. The process of claim 1 wherein said molar ratio is (0.015 to 0.060):1.

7. The process of claim 6 wherein said molar ratio is (0.022 to 0.055):1.

8. The process of claim 1 wherein said support comprises calcium silicate, magnesium silicate, aluminum silicate, alumina, silica, kieselguhr, or mixtures thereof.

9. The process of claim 8 wherein said support comprises alumina, silica, kieselguhr, or mixtures thereof.

10. The process of claim 9 wherein said support comprises silica and/or kieselguhr.

11. The process of claim 10 wherein said support is kieselguhr.

12. The process of claim 1 wherein said conversion is carried out at a conversion temperature of 150° to 300° C.

13. The process of claim 12 wherein said conversion temperature is 180° to 280° C.

14. The process of claim 13 wherein said conversion temperature is 200° to 260° C.

15. The process of claim 2 wherein said pressure is 0.1 to 1 MPa.

16. The process of claim 15 wherein said pressure is 0.15 to 0.8 MPa.

17. The process of claim 16 wherein said pressure is 0.15 to 0.6 MPa.

* * * * *